United States Patent [19]

Wang et al.

[11] Patent Number: 5,869,671
[45] Date of Patent: Feb. 9, 1999

[54] PROCESS FOR PREPARING AN ANGIOTENSIN CONVERTING ENZYME INHIBITOR

[75] Inventors: Shin-Shin Wang, Hsinchu; Hui-Ping Tsai, Changhua, both of Taiwan

[73] Assignee: Industrial Technology Research Institute, Hsinchu, Taiwan

[21] Appl. No.: 106,288

[22] Filed: Jun. 29, 1998

[51] Int. Cl.$^6$ .................................................. C07D 217/00
[52] U.S. Cl. ............................................ 546/147; 548/533
[58] Field of Search ............................... 548/533; 546/147

[56] References Cited

U.S. PATENT DOCUMENTS 4,808,741  2/1989  Dudenes ................................... 556/418
5,359,086  10/1994  Merslavic ................................. 548/533

OTHER PUBLICATIONS

Chem abstract 1988:187285; abstract of JP 62048655.

*Primary Examiner*—Samuel Barts
*Attorney, Agent, or Firm*—Sughrue, Mion, Zinn, Macpeak & Seas, PLLC

[57] ABSTRACT

A process for preparing an angiotensin converting enzyme inhibitor. Phosphorus pentachloride is reacted with the carboxylic acid group of an amino acid to form an acyl chloride hydrochloride. The resulting hydrochloride salt is then coupled with a silylated amino acid in a non-aqueous medium to form a high yield peptide. The peptide is used as an angiotensin converting enzyme (ACE) inhibitor.

18 Claims, No Drawings

PROCESS FOR PREPARING AN ANGIOTENSIN CONVERTING ENZYME INHIBITOR

BACKGROUND OF THE INVENTION

1. Field of the Invention

The present invention relates to a process for preparing an angiotension converting enzyme (ACE) inhibitor, and in particular to a process for preparing angiotension converting enzyme inhibitors such as intermediates of captopril, enalapril, quinapril and the like without using phosgene, diphosgene and triphosgene.

2. Description of the Related Arts

The synthesis of enalapril, an angiotensin coverting enzyme inhibitor which is used among other things in the treatment of blood pressure, by coupling amino acids has been disclosed in many patents. For example, in European Patent No. 0215335, enalaprils are prepared by reacting N-[(s-ethoxycarbonyl-3-phenyl-propyl]-L-alanine with phosgene to form N-carboxylanhydride, followed by condensation with L-proline. This process uses noxious phosgene.

U.S. Pat. No. 5,359,086 discloses a process for the preparation of enalapril. According to the process, alkyl-L-alanine is reacted with a coupling agent, N,N-carbonyldiimidazole to form alkyl-L-alanine-N-carboxy anhydride. The alkyl-L-alanine-N-carboxy anhydride is then coupled with L-proline silyl ester hydrochloride to form the enalapril. The coupling agent, N,N-carbonyldiimidazole, is expensive.

In Spain Patent No. 544781, a process for preparing enalapril has been proposed. The process involves reacting alkyl-L-alanine with N-hydroxysuccinimide and dicyclohexylcarbodiimide (DCC) to form N'-succinimidyl ester and coupling the N'-succinimidyl ester with L-proline. However, it is hard to remove DCC.

U.S. Pat. No. 4,808,741 discloses a process for preparing pharmaceutically active carboxylalkyl dipeptides such as enalapril, lisinopril and the like. In the process, the amino acid group of a L-proline is protected with a benzyl protecting group. Subsequently, the protecting group is removed.

SUMMARY OF THE INVENTION

It is therefore an object of the invention to provide a safe process for preparing angiotensin converting enzyme inhibitors such as enalapril, quinapril, delapril and ramipril by avoiding the use of noxious phosgene, diphosgene and triphosgene.

The object of the invention is achieved by using a non-expensive and safe coupling agent, phosphorus pentachloride. It is found that the phosphorus pentachloride can activate the carboxylic acid group of an amino acid to form acyl chloride and, in the mean time, protect the amino group, thereby leading to the formation of a hydrochloride salt. The resulting hydrochloride salt can be coupled further with a silylated amino acid in a non-aqueous medium to form peptide. When using this process to synthesize enalapril, the yield can be as high as 96%.

DETAILED DESCRIPTION OF THE INVENTION

Generally, the process of the invention can be used to prepare an ACE inhibitor of the following formula (I):

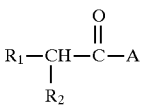

wherein $R_1$ represents

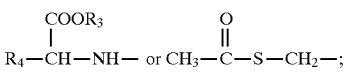

$R_2$ represents $C_1$–$C_6$ alkyl;
$R_3$ represents $C_1$–$C_6$ alkyl, phenyl or phenylmethyl;
$R_4$ represents phenyl($C_1$–$C_6$)alkyl, phenyl or $C_1$–$C_6$ alkyl; and
A represents amino acid residue.

According to the process, the compound of formula (III):

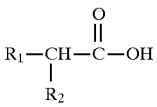

wherein $R_1$ and $R_2$ are defined as above, is first activated by phosphorus pentachloride in a non-aqueous medium at a temperature of $-10°$ C.–$0°$ C. to form a hydrochloride salt of acyl chloride of formula (II):

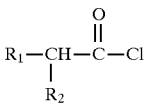

The compound II is then subjected to condensation with a silylated amino acid in a non-aqueous medium at a temperature of $-10°$ C.–$0°$ C. When the condensation reaction is complete, water is added to stop the reaction. After extraction with an organic solvent such as dichloromethane or ethyl acetate, drying and concentration, ACE inhibitors of compound I can be obtained in high yield.

The group of non-aqueous mediums suitable for use in the invention includes but is not limited to acetone, acetonitrile, dioxan, methylene chloride and tetrahydrofuran.

The silylated amino acid can be silylated proline, the derivatives thereof, or silylated 1,2,3,4-tetrahydroisoquinoline-3-carboxylic acid. The silylated amino acid is prepared by reacting an amino acid with hexamethylsilazane (HMDS), chlorotrimethylsilane and bis (trimethylsilyl)acetamide (BSA).

In the preparation of enalapril, N-[1(S)-ethoxycarbonyl-3-peheylporopyl]-L-alanine (compound III, wherein $R_1$ is

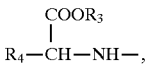

$R_2$ is methyl, $R_3$ is ethyl and $R_4$ is phenylethyl) is reacted with phosphorus pentachloride, followed by condensation with a silylated proline. The acyl chloride of the L-alanine can be coupled with other amino acids using phosphorus pentachloride as a coupling agent to form various ACE inhibitors such as quinapril, imidapril, ramipril and spirapril.

The following examples are intended to demonstrate the invention more fully without acting as a limitation upon its scope, since numerous modifications and variations will be apparent to those skilled in this art.

EXAMPLE 1

Synthesis of N-[N-(1-(S)-ethoxycarbonyl-3-phenylpropyl)-L-alanyl]-L-proline 1 g (3.6 mmole) of (2S)-2-[N-1-(ethoxycarbonyl)-2-benzoyl]ethyl amino propionate was added to a reaction flask containing 1.27 g(6 mmole) of phosphorus pentachloride and 3 ml of methylene chloride by using a solid addition funnel, and agitated at 0° C. for 6 hours. 6 ml of heptane was then added, and a white solid precipitated. The resulting suspension was filtrated and the cake was washed with heptane giving N-[1-(S)-ethoxycarbonyl-3-phenylpropyl]-L-alanine acid chloride.

L-proline, in the amount of 0.48 g(4.0 mmol), bis (trimethylsilyl)acetamide (BSA), in the amount of 1 ml (4.0 mmol), and 4 ml of methylene chloride were placed in a 25 ml three-neck reaction flask. The reaction mixture was then agitated at room temperature until the solution became clear. 0.5 ml (3.6 mmol) of triethylamine was then added and the temperature was lowered to −10° C. 4 ml of methylene chloride and the L-alanine acid chloride were then mixed and dropped into the reaction flask and agitated at −10° C. for 30 minutes. 6 ml of water was then added to stop the reaction. 3M hydrochloric acid was then added to the resulting solution to adjust the pH to about 3. After extracting with methylene chloride(10 ml×3) and drying over magnesium sulfate and concentrating by a vacuum concentrator, 1.26 g (3.43 mmol) of the title compound was obtained as a colorless liquid in a 96% yield.

1.26 g of the obtained title compound and 0.34 g (2.9 mmol) of maleic acid were heated and dissolved in 10 ml of ethyl acetate. After standing at room temperature for 7 hours, filtering and drying, 0.86 g of the salt of the title compound was obtained.

$^1$HNMR(400 MHz, CD$_3$OD): δ7.18–7.31 (m,5H), 6.25(s, 2H), 4.51(dm, 1H), 4.26–4.34(m,2H), 4.23(dq,1H), 3.89(dt, 1H), 3.54–3.68 (m,2H), 2.70–2.86(m,2H), 2.19–2.36(m, 4H), 1.98–2.07(m,2H),1.54(dd,3H), 1.32(t,3H).

EXAMPLE 2

Synthesis of N-[N-(1-(S)-ethoxycarbonyl-3-phenylpropyl)-L-alanyl]-L-proline 5 ml of methylene chloride was added to a reaction flask containing 1.27 g (6 mmol) of phosphorus pentachloride. The temperature was then lowered to −10° C. and 1 g (3.6 mmol) of N-[1-(S)-ethoxycarbonyl-3-phenylpropyl]-L-alanine was added using a solid addition funnel. The reaction solution was then allowed to react at 0° C. for 5 hours. 8 ml of heptane was added and stirred for 30 minutes. The solid obtained after filtration was dissolved in 10 ml of methylene chloride.

6 ml of methylene chloride and 0.97 ml (7.6 mmol) of chlorotrimethyl silane were added to a separate reaction flask containing 0.48 g (4 mmol) of L-proline. The reaction mixture was allowed to react for 1.5 hours at room temperature and then 1.54 ml(11 mmol) of triethylamine was added and the temperature was lowered to −10° C. The L-alanine acid chloride was then added into the reaction flask and stirred at 0° C. for 1 hour. 10 ml of water was then added and stirred. After extracting with methylene chloride, drying and concentrating, the title compound was obtained in a 76.4% yield. The NMR spectra data was the same as that obtained in Example 1.

EXAMPLE 3

Synthesis of N-[N-(1-(S)-ethoxycarbonyl-3-phenylpropyl)-L-alanyl]-L-proline 5 ml of methylene chloride was added to a reaction flask containing 1.27 g (6 mmol) of phosphorus pentachloride. The temperature was then lowered to −10° C. and 1 g (3.6 mmol) of N-[1-(S)-ethoxycarbonyl-3-phenylpropyl]-L-alanine was added using a solid addition funnel. The reaction solution was then allowed to react at 0° C. for 5 hours. 8 ml of heptane was added and stirred for 30 minutes. The solid obtained after filtration was dissolved in 10 ml of methylene chloride.

4 ml of methylene chloride and 0.86 ml (4.1 mmol) of hexamethyldisilazane, HMDS) were added to a separate reaction flask containing 0.48 g (4 mmol) of L-proline. The reaction mixture was refluxed for 30 minutes and then lowered to room temperature. 0.52 ml(3.7 mmol) of triethylamine was then added and the temperature was lowered again to −10° C. The L-alanine acid chloride was then added into the reaction flask and stirred at 0° C. for 1 hour. 10 ml of water was then added and stirred. After extracting with methylene chloride, drying and concentrating, the title compound was obtained in a 79.4% yield. The NMR spectra data was the same as that obtained in Example 1.

EXAMPLE 4

Synthesis of quinapril 5 ml of methylene chloride was added to a reaction flask containing 1.27 g (6 mmol) of phosphorus pentachloride. The temperature was then lowered to 0° C. and 1 g (3.6 mmol) of N-[1-(S)-ethoxycarbonyl-3-phenylpropyl]-L-alanine was added using a solid addition funnel. The reaction solution was then allowed to react at room temperature for 4 hours. 8 ml of heptane was added and stirred for 30 minutes. The solid obtained after filtration was dissolved in 10 ml of methylene chloride.

4 ml of methylene chloride and 2 ml (8 mmol) of BSA were added to a separate reaction flask containing 0.74 g (4.2 mmol) of (S)-(−)-1,2,3,4-tetrahydroisoquinoline-3-carboxylic acid. The reaction mixture was allowed to react at room temperature for 2 hours. 0.52 ml(3.7 mmol) of triethylamine was then added and the temperature was lowered to 0° C. The L-alanine acid chloride was then added into the reaction flask and stirred at room temperature overnight. 10 ml of water was then added and stirred. After extracting with methylene chloride, drying and concentrating, the title compound was obtained in a 83.9% yield.

$^1$HNMR (400 MHz, CD$_3$OD): δ7.14–7.30 (m, 9H), 4.13–4.24 (m,2H), 3.90–4.02 (m,2H), 3.61(dt, 1H), 3.20(q, 2H),2.87–2.96(m,2H), 2.44–2.71(m, 2H), 1.59–1.67(m,2H), 1.50(d,3H, 1.25(t,3H. MS(m/e): 439(M+1).

EXAMPLE 5

Synthesis of (S)-1-(3-acetylthio-2-methyl-oxopropyl)-L-proline 5 ml of methylene chloride was added to a reaction flask containing 1.27 g (6 mmol) of phosphorus pentachloride. The temperature was then lowered to 0° C. and 0.58 g (3.6 mmol) of (S)-3-acetylthio-2-methyl propanic acid was added using a solid addition funnel. The reaction solution was then allowed to react at room temperature for 5 hours. The solvent was evaporated and 10 ml of heptane was added to the residue.

4 ml of methylene chloride and 1 ml (4 mmol) of BSA were added to a separate reaction flask containing 0.48 g (4 mmol) of L-proline. The reaction mixture was allowed to react at room temperature for 1 hour. 0.52 ml(3.7 mmol) of triethylamine was then added and the temperature was lowered to 0° C. The methylene chloride solution was then added into the reaction flask and stirred at room temperature overnight. 10 ml of water was then added and stirred After extracting with methylene chloride, drying and concentrating, the title compound was obtained in a 77.9% yield.

$^1$HNMR(200 MHz, CDCl$_3$): δ 10.57 (s,1H), 4.34 (dt, 1H), 3.5–3.6 (m, 2H), 3.06–3.12 (m, 2H), 2.6–2.9 (dq, 1H), 2.27(s,3H), 1.96–2.15(m, 4H), 1.21(d, 3H). MS(m/e): 260 (M+1).

What is claimed is:

1. A process for preparing a compound of the formula (I):

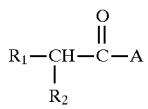  I wherein R$_1$ represents

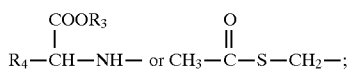

R$_2$ represents C$_1$–C$_6$ alkyl;
R$_3$ represents C$_1$–C$_6$ alkyl, phenyl or phenylmethyl;
R$_4$ represents phenyl(C$_1$–C$_6$)alkyl, phenyl or C$_1$–C$_6$ alkyl; and
A represents amino acid residue;
comprising the following steps:
(a) reacting a compound of formula (III):

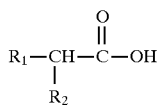  III wherein R$_1$ and R$_2$ are defined as above;
with phosphorus pentachloride to obtain a compound of formula (II):

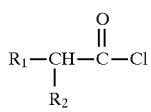  II wherein R$_1$ and R$_2$ are defined as above; and
(b) reacting the compound of formula (II) with a silylated amino acid in a non-aqueous medium.

2. The process as claimed in claim 1, wherein the non-aqueous medium is an organic solvent selected from the group consisting of acetone, acetonitrile, dioxan, methylene chloride and tetrahydrofuran.

3. The process as claimed in claim 2, wherein said organic solvent is methylene chloride.

4. The process as claimed in claim 1, wherein the reaction is carried out at a temperature of −10° C. to 0° C.

5. The method as claimed in claim 1, wherein the compound of formula (I) is a compound wherein R$_1$ is

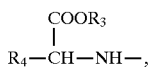

R$_2$ represents methyl, R$_3$ represents ethyl and R$_4$ represents phenylethyl.

6. The method as claimed in claim 1, wherein said silylated amino acid is a silylated proline or the derivatives thereof.

7. The method as claimed in claim 6, wherein said silylated proline is prepared by reacting proline with a compound selected from the group consisting of hexamethylsilazane (HMDS), chlorotrimethylsilane and bis (trimethylsilyl)acetamide (BSA).

8. The method as claimed in claim 1, wherein said silylated amino acid is a silylated 1,2,3,4-tetrahydroisoquinoline-3-carboxylic acid.

9. The method as claimed in claim 1, wherein the compound of formula (I) is a compound wherein R$_1$ is

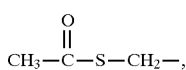

R$_2$ represents methyl, R$_3$ represents ethyl and R$_4$ represents phenylethyl.

10. A process for preparing a compound of the formula (I):

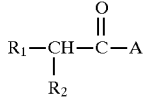  I wherein R$_1$ represents

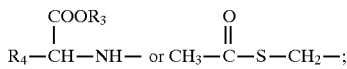

R$_2$ represents C$_1$–C$_6$ alkyl;
R$_3$ represents C$_1$–C$_6$ alkyl, phenyl or phenylmethyl;
R$_4$ represents phenyl(C$_1$–C$_6$)alkyl, phenyl or C$_1$–C$_6$ alkyl; and
A represents amino acid residue;
comprising reacting a compound of formula (II):

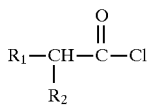  II wherein R$_1$ and R$_2$ are defined as above;
with a silylated amino acid in a non-aqueous medium.

11. The process as claimed in claim 10, wherein the non-aqueous solution is an organic solution selected from the group consisting of acetone, acetonitrile, dioxan, methylene chloride and tetrahydrofuran.

12. The process as claimed in claim 11, wherein said organic solvent is methylene chloride.

13. The process as claimed in claim 10, wherein the reaction is carried out at a temperature of −10° C. to 0° C.

14. The method as claimed in claim 10, wherein the compound of formula (I) is a compound wherein R$_1$ is

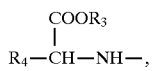

$R_2$ represents methyl, $R_3$ represents ethyl and $R_4$ represents phenylethyl.

15. The process as claimed in claim 10, wherein said silylated amino acid is a silylated proline or the derivatives thereof.

16. The process as claimed in claim 15, wherein said silylated proline is prepared by reacting proline with a compound selected from the group consisting of hexamethylsilazane (HMDS), chlorotrimethylsilane and bis(trimethylsilyl)acetamide (BSA).

17. The process as claimed in claim 10, wherein said silylated amino acid is a silylated 1,2,3,4-tetrahydroisoquinoline-3-carboxylic acid.

18. The process as claimed in claim 10, wherein the compound of formula (I) is a compound wherein $R_1$ is

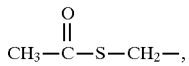

$R_2$ represents methyl, $R_3$ represents ethyl and $R_4$ represents phenylethyl.

* * * * *